United States Patent [19]

Caccavo

[11] Patent Number: 4,943,992
[45] Date of Patent: Jul. 24, 1990

[54] PEDIATRIC X-RAY POST

[76] Inventor: Joseph F. Caccavo, 31 West Boulevard, East Rockaway, N.Y. 11518

[21] Appl. No.: 233,223

[22] Filed: Aug. 18, 1988

[51] Int. Cl.$^5$ ............................................. H05G 1/00
[52] U.S. Cl. .................................... 378/208; 378/177; 378/180
[58] Field of Search ............... 378/177, 180, 203–204, 378/208–209, 156, 159; 250/515.1

[56] References Cited

U.S. PATENT DOCUMENTS

| | | | |
|---|---|---|---|
| 3,178,574 | 4/1965 | Stryker | 378/177 |
| 3,215,834 | 11/1965 | Tayman | 378/180 |
| 3,723,743 | 3/1973 | Brackenbrough et al. | 250/515.1 |
| 3,944,838 | 3/1976 | Gäde | 250/515.1 |
| 3,967,128 | 6/1976 | Smulewicz | 378/180 |
| 4,669,106 | 5/1987 | Ammerman | 378/208 |
| 4,698,837 | 10/1987 | Van Steenburg | 378/208 |

Primary Examiner—Craig E. Church
Assistant Examiner—John C. Freeman
Attorney, Agent, or Firm—Burton E. Levin

[57] ABSTRACT

Apparatus is described for immobilizing a child and shielding its gonads during X-ray examination. The child is held on the upper surface of an X-ray transparent horizontal platform with its legs straddling a vertical post bearing a laterally extending lead shield. The lead shield is both vertically and horizontally positionable so as to permit precise and close spacing above the child's body. The lower surface of the child supporting platform is flanged to provide a frame which retains an X-ray film cassette and minimizes blurring resulting from the child's movement. A gonadal shield assembly which is suitable for both male and female children has a generally triangular sheet of lead mounted on a rotatable X-ray transparent plate which is supported by an X-ray transparent arm extending laterally from the post.

7 Claims, 3 Drawing Sheets

PEDIATRIC X-RAY POST

BACKGROUND OF THE INVENTION

1. Field of the Invention

This invention relates generally to means for restraining the movement of a child during X-ray examination and for protecting selected areas on the child's body from X-ray radiation. More specifically, it relates to apparatus which facilitates such restraint while an X-ray photograph of the hip is being taken and which shields the gonads of that child from radiation.

2. Description of the Prior Art

Recent and continuing improvements in the sensitivity of X-ray film emulsions have greatly increased resolution and dramatically reduced the X-ray radiation intensity required to produce useful images of the human body. However, even such low intensity radiation is known to be potentially harmful and it is established practice to limit exposure to only those portions of the body which must be imaged. This commonly is accomplished with adult patients by covering the non-target portions of the body with a blanket containing a radiation opaque material such as lead. This, however, is not always a practical method of shielding the gonads during X-ray examinations of the hip, lower spine or other portion of the pelvic region.

In such examinations, the patient is positioned supine on an X ray examination table with its Pelvic region below the X-ray tube and directly above a drawer in the table which contains an X-ray film cassette. Generally, anterior/posterior or AP exposures are made in two positions; i.e., with the legs extended and parallel and with the legs extended in a frog leg position so that they are separated by approximately 90°. Protection of the gonads is provided by a lead shield which is attached to the X-ray tube assembly and is held close beneath the tube so as to cast a downward shadow.

Since the X-ray tube generally is a meter or more above the examination table, the position of the shield must be very careful adjusted to properly focus the shadow on the patient's gonads. The patient must remain motionless from the time it is positioned on the examination table until the X-ray tube discharge, as even a small movement could expose the gonads or blur the film image. While adults are capable of remaining motionless for prolonged periods, infants and most small children are not.

In order to reduce the possibility that child movement might expose its gonads to radiation or that it might blur the X-ray film image, it is customary to place the child on its back directly on the X-ray film cassette and to have a parent grasp its thighs to hold its legs extended and flat against the cassette for the time required to focus the tube mounted gonadal shield and to expose the film. This not only unnecessarily exposes the hands and arms of the parents to radiation, but is not always totally effective in preventing either film blurring or undesirable exposure of the gonads of a squirming child.

SUMMARY OF THE INVENTION

It is an object of this invention to provide more effective means for restraining the movement of a child during an X-ray examination. It is a further object to provide improved means for shielding that child from unecessary radiation exposure. It is a more specific object to provide apparatus uniquely suited for use in a pediatric hip X-ray examination which effectively couples an X-ray film cassette and a lead gonadal shield to the pelvic region of a substantially immobilized child, thereby minimizing the possibility that squirming by the child will expose its gonads to radiation or blur the film image. These and other objects, which will be apparent to those skilled in the art from this disclosure, are accomplished by this invention.

This invention arose from the observation that lower body movement of a child can effectively be restrained without risk of injury by placing that child on its back with its legs straddling a fixed vertical post and extending the legs by pulling gently on the child's feet.

Thus, one broad aspect of this invention is apparatus for restraining lower body movement of a child during an X-ray examination comprising a flat X-ray transparent platform, said platform being adapted to be positioned between said child and X-ray detection means and to support said child, and a straddling post for said child, said post being firmly held normal to the child supporting surface of said platform.

It also has been found that blurring of an X-ray image resulting from sudden violent movement of a child as the X-ray tube is discharged can be minimized when detection means, such as an X-ray film, is physically coupled to the child supporting platform of this invention and the child is thereby rendered immobile relative to post, platform and film.

A second broad aspect of this invention is the apparatus described above wherein said X-ray detection means is an X-ray film and said platform is adapted to firmly hold said film parallel to said child supporting surface.

In addition, it has been found that an X-ray shield, such as a gonadal shield, which is supported by a straddling post of this invention can be properly positioned much faster than a prior art tube mounted shield. Furthermore, the proximity to the child of such post mounted shield, coupled with the relative immobility of the child with respect to both the post and shield, greatly reduces the danger of undesirable exposure resulting from a sudden violent movement as the X-ray tube discharges.

Thus, still another aspect of this invention is a platform mounted straddling post, as described above, wherein said post supports a laterally extending X-ray opaque shield which is adapted to be positioned between a source of X-ray radiation and a selected area on the body of said child.

DESCRIPTION OF THE PREFERRED EMBODIMENTS

Figure 1:
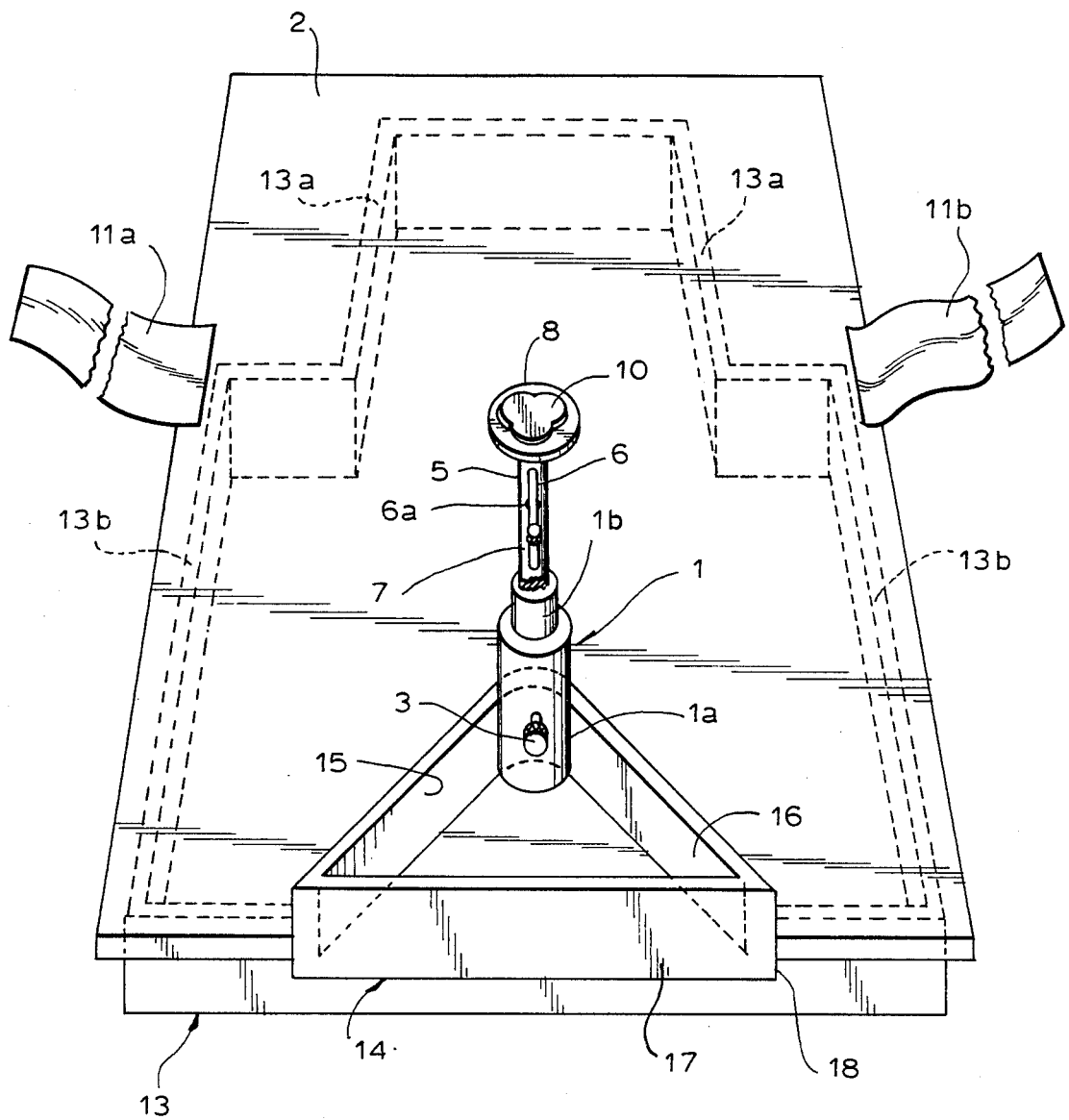
FIG. 1 is a Perspective view, partially cut away, of a pediatric restraining and X-ray shielding apparatus of this invention in which a straddling post holds an adjustably positionable gonadal shield above a child supporting platform and the platform is flanged on its lower side to retain an X-ray film cassette.
Figure 2:
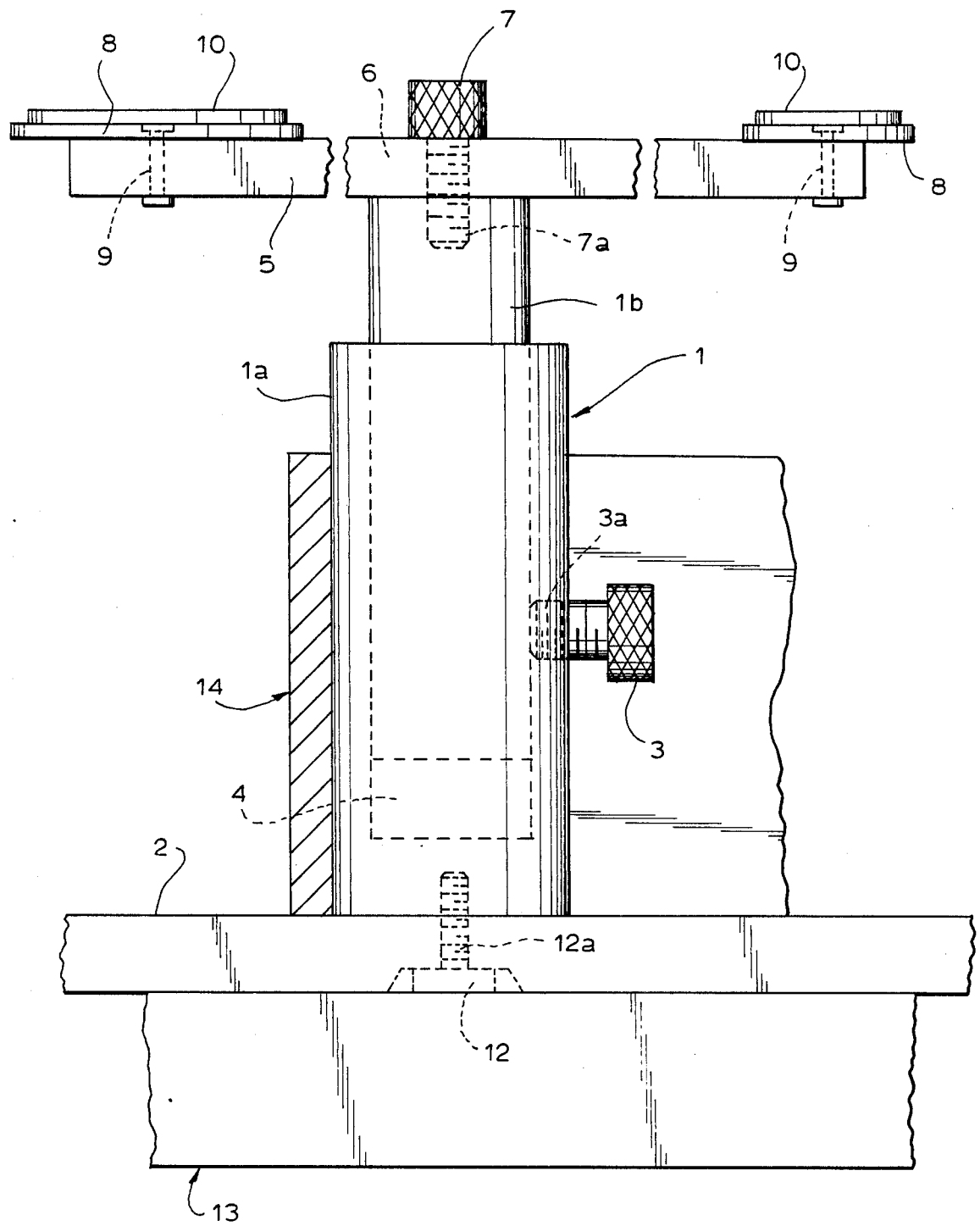
FIG. 2 is a partial side elevation view of the apparatus of FIG. 1 showing details the telescoping straddling post and the laterally extending arm bearing the gonadal shield.
Figure 3:
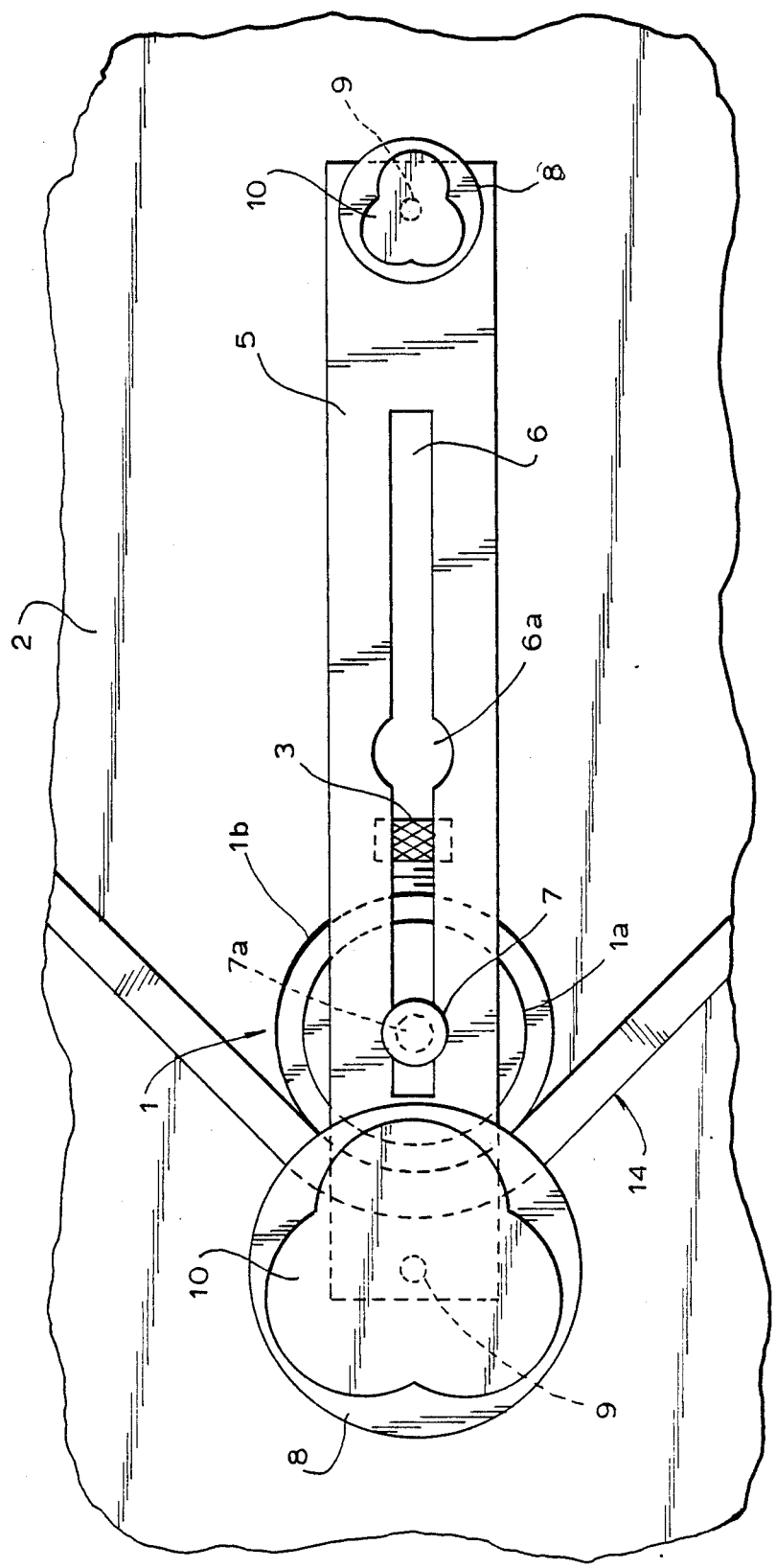
FIG. 3 is partial plan view of the apparatus of FIG. 1 showing details of the gonadal shield and its support arm.

FIGS. 1 through 3 show especially preferred apparatus of this invention which is designed for use during X-ray examination of the hip of an infant or other small child.

A telescoping pediatric straddling post 1 stands vertically on the upper surface of rectangular platform 2, which is made of poly (methylmethacrylate) or other rigid X-ray transparent material. Post 1 is most advantageously located in the lower third of the platform as it is illustrated in FIG. 1 and is centered between the long sides. As shown most clearly in FIG. 2, post 1 is held securely by threaded fastener 12 which extends through a hole 12a in platform 2 and engages a threaded opening 12b in the base of fixed outer post segment 1a.

Fixed outer post segment 1a has a circular recess 4 into which mating post segment 1b fits loosely, thereby providing the aforementioned telescoping capacity. Segment 1b can be held in a desired position by tightening set screw 3 which engages threaded opening 3a in post segment 1a and bears on post segment 1b.

As can be seen most clearly in FIGS. 2 and 3, arm 5, which is made of poly (methylmethacrylate) or other rigid X-ray transpatent material, is held to the top of movable post segment 1b by set screw 7 which extends through slot 6 in arm 5 and engages threaded opening 7a in the top end of fixed post segment 1b. As shown in FIG. 3, an enlarged section 6a of slot 6 is larger than the head of set screw 7 and permits the removal of arm 5 without completely disengaging set screw 7. A disk B, which also is made of poly (methylmethacrylate) or other rigid X-ray transparent material, is rotatably mounted on a pin 9 extending through each end of arm 5. Each disk B supports a different size lead sheet gonadal shield 10 which advantageously has a generally triangular shape, such as the clover leaf shape shown here. One end of arm 5, as well as one disk 8 and shield 10, has been omitted from FIG. 1 for clarity.

Referring again to FIG. 1, platform 2 has bonded to its lower surface a T-shape frame 13 which is designed to fit snugly around and retain a conventional rectangular X-ray film cassette in either of two positions; i.e., with frame segments 13a abutting the long sides of the cassette or, when the cassette is rotated 90°, with frame segments 13b abutting the short sides of the cassette.

Upper body restraining straps 11a and 11b are firmly held to the edges of platform 2 in the upper third of the platform as shown in FIG. 1. Advantageously, these straps are made of nylon with a semi-rigid hook and loop surface so that they adhere when overlapped. Such material is commercially available under the trademark Velcro.

Removable triangular frame 14 has two equal length legs 15 and 16, which are positioned 90° apart and a long leg 17 having a lip 18. As shown in FIG. 1, frame 14 is securely held in position on the surface of platform 2 by resting the inner surfaces of short legs 15 and 16 against post 1 and slipping lip 18 over the edge of platform 2. It can quickly be removed by slipping lip 18 out of engagement with the edge of platform 2 and lifting frame 14 over post 1 and arm 5.

The apparatus described above may be used simply by placing it on a conventional X-ray table with the X-ray film cassette within frame 13 on the underside of platform 2, rather than in the drawer beneath the table. For examination in the parallel leg position, triangular frame 14 is removed and the child is placed on its back on platform 2 with its legs straddling post 1. The child is immobilized by securing straps 11a and 11b across its chest and having an adult hold its feet together and pull gently to hold the child's crotch firmly against post 1 and extend its legs. For examination in the frog leg position, triangular frame 14 is placed over post 1 and lip 18 is slipped over the edge of platform 2. The child is similarly positioned with straps 11a and 11b secured and the adult pulls gently on the feet to extend the child's legs while maintaining them in contact with the legs 15 and 16 of frame 14.

Once the child is so immobilized, the X-ray tube is placed above its pelvic region and the gonadal shield is positioned between the X-ray tube and the child's gonads. This is quickly accomplished in a few simple steps.

First, the shield 10 which is the most appropriate size for the child is selected and the disk S which supports that selected shield is rotated so that an angle of that generally triangular shield faces faces toward the post for a female child, as illustrated in FIGS. 1 and 3, or away from the post for a male child. It generally is desirable that the shield be just large enough to shadow the entire reproductive system and bladder of the child.

Next, set screw 7, which extends through slot 6 in arm 5, is loosened permitting arm 5 to be rotated to place the selected shield 10 above the child. This also permits arm 5 to be moved longitudinally to properly position that selected shield immediately above the gonads. Tightening set screw 7 locks shield 10 in that proper position.

Finally, shield 10 is positioned vertically by loosening set screw 3 in fixed post segment 1a, lowering movable post segment 1b until arm 5 touches or is immediately above the child's abdomen and then tightening set screw 3.

A child restrained by this apparatus effectively has its pelvic region physically coupled to both the X-ray film cassette and the closely positioned gonadal shield, so that even a sudden violent movement by the child is accompanied by corresponding movement of the cassette and shield. The inability of the child to significantly change the position of its pelvic region relative to the cassette and shield greatly reduces both the risk of exposure of its gonads to radiation and the inconvenience of film blurring. In addition, since the child can be immobilized by a parent holding only its feet, the use of this apparatus also reduces unnecessary exposure to radiation of that parent's hands and arms.

It will, of course, be understood that various modifications and additions may be made in the preferred embodiment of the invention described above without departing from the spirit and scope of the invention as defined in the claims below. For example, it will be apparent that the pediatric straddling post of this invention could be utilized in conjunction with a conventional X-ray examination table having a film cassette drawer by mounting the post at an end of an elongated flat base which is clamped, at its other end, to an edge of the table. Similarly, it will be apparent that different shapes and sizes of lead shields could be supported, by a variety of means, by the post in order to protect various selected areas of the child's body or that the frame on the underside of the X-ray transparent child supporting platform could be sized to snugly retain any size X-ray film cassette in any desired position or positions.

I claim;

1. Apparatus for immobilizing and protecting a child during an X-ray examination comprising (a) a horizontal flat platform to support said child, said platform being made of an X-ray transparent material and having a frame extending beneath its lower surface to retain an X-ray film cassette, (b) a pediatric post for straddling by said child, said post being securely held normal to the upper surface of said platform and (c) a lead shield supported by an arm extending laterally from said post, said arm having a longitudinal slot and being held at the upper end of said post by a threaded fastener extending through said for positioning said shield between a source of X-ray radiation and the gonads of said child.

2. Apparatus of claim 1 wherein said frame is T-shape so as to accomodate said X-ray film cassette in two positions.

3. Apparatus of claim 1 wherein said arm supports a rotatable plate bearing a generally lead sheet gonadal shield, said arm and said plate being X-ray transparent.

4. Apparatus of claim 1 including a strap attached to said platform for restraining upper body movement of said child.

5. Apparatus of claim 1 wherein the position of said shield is vertically adjustable with respect to said horizontal flat platform.

6. Apparatus of claim 5 wherein said arm is attached to the upper end of said post and said post is telescoping.

7. Apparatus for immobilizing a child during an X-ray examination comprising (a) a horizontal flat platform to support said child, said platform being made of an X-ray transparent material and having a frame extending beneath its lower surface to retain an X-ray film cassette, (b) a pediatric post for straddling by said child, said post being securely held normal to the upper surface of said platform and (c) a triangular frame having two equal length short legs positioned 90° apart and a long leg having a lip, said triangular frame being held firmly on said upper surface of said platform by resting the inner surfaces of said short legs against said post and resting said lip against an edge of said platform.

* * * * *